United States Patent [19]
Ueno et al.

[11] Patent Number: 5,340,733
[45] Date of Patent: Aug. 23, 1994

[54] MBOI RESTRICTION-MODIFICATION GENES

[75] Inventors: Takashi Ueno, Otsu; Hiroyuki Ito, Sapporo; Hirokazu Kotani, Moriyama; Kazuo Nakajima, Kyoto, all of Japan

[73] Assignee: Takara Shuzo Co., Ltd., Kyoto, Japan

[21] Appl. No.: 7,775

[22] Filed: Jan. 22, 1993

[30] Foreign Application Priority Data

Feb. 3, 1992 [JP] Japan .................................. 4-46366
Jan. 8, 1993 [JP] Japan .................................. 5-16828

[51] Int. Cl.$^5$ ........................ C12N 9/22; C12N 9/10; C12N 15/55
[52] U.S. Cl. ................................. 435/199; 435/193; 435/320.1; 435/252.33; 536/23.2
[58] Field of Search .................... 435/199, 193, 320.1, 435/252.33; 536/23.2

[56] References Cited

PUBLICATIONS

J. Mol. Biol. 114 pp. 169–179 (1977) "Two Sequence-specific Endonucleases from *Moraxella bovis*."

*Primary Examiner*—Charles L. Patterson, Jr.
*Attorney, Agent, or Firm*—Wenderoth, Lind & Ponack

[57] ABSTRACT

To provide MboI restriction-modification genes and a method for producing MboI restriction enzyme and MboI modification enzyme by using a novel microorganism having, introduced thereinto, plasmids containing said genes. A method for producing MboI restriction enzyme and/or MboI modification enzyme which comprises incubating a microorganism carrying plasmids having, integrated thereinto, MboI restriction-modification genes, and recovering the MboI restriction enzyme and/or MboI modification enzyme thus produced from the culture. It becomes possible to efficiently produce MboI restriction enzyme and/or MboI modification enzyme which are useful in the field of genetic engineering.

8 Claims, 1 Drawing Sheet

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL:

( i v ) ANTI-SENSE:

( v ) FRAGMENT TYPE: N-terminal fragment

( v i ) ORIGINAL SOURCE:
        ( A ) ORGANISM: Moraxella bovis
        ( B ) STRAIN: ATCC 10900
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

```
        ( i x ) FEATURE:
                ( A ) NAME/KEY:
                ( B ) LOCATION: 32
                ( C ) IDENTIFICATION METHOD:
                ( D ) OTHER INFORMATION: /note="not identified"

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:1:

Met Lys Leu Ala Phe Asp Asp Phe Leu Asn Ser Met Ser Glu Thr
 1               5                  10                  15

Asn Thr Thr Leu Asp Tyr Phe Thr Asp Phe Asp Lys Val Lys Lys
                20                  25                  30

Asn Xaa Ala Gln ( 2 ) INFORMATION FOR SEQ ID NO:2:

( i ) SEQUENCE CHARACTERISTICS:
                ( A ) LENGTH: 23 bases
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE: N-terminal fragment ( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION: 12
                ( C ) IDENTIFICATION METHOD:
                ( D ) OTHER INFORMATION: /note="inosine"

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
```

(J) PUBLICATION DATE:
(K) RELEVANT RESIDUES IN SEQ ID NO:

(xi) SEQUENCE DESCRIPTION: SEQ ID NO:2:

GATTATTTTA CNGATTTTGA TAA          23

(2) INFORMATION FOR SEQ ID NO:3:

(i) SEQUENCE CHARACTERISTICS:
(A) LENGTH: 2659 base pairs
(B) TYPE: nucleic acid
(C) STRANDEDNESS: double
(D) TOPOLOGY: linear (ii) MOLECULE TYPE: genomic DNA (iii) HYPOTHETICAL:

(iv) ANTI-SENSE:

(v) FRAGMENT TYPE:

(vi) ORIGINAL SOURCE:
(A) ORGANISM: Moraxella bovis
(B) STRAIN: 10900
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION: 12
(C) IDENTIFICATION METHOD:
(D) OTHER INFORMATION: /note="inosine"

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:3:

```
G AAT TCT TTG CTT GAT GAA ATT CAA AAA CGC TTG CCT GAT TTT GTT        46
  Asn Ser Leu Leu Asp Glu Ile Gln Lys Arg Leu Pro Asp Phe Val
   1               5                  10                  15

CAC TCA CAA GAT TTT TGT TTG GTA GAG CCT TTT GTT GGT GGT GGG          91
His Ser Gln Asp Phe Cys Leu Val Glu Pro Phe Val Gly Gly Gly
                 20                  25                  30

GCG GTG TCC TTA TGG GCA TTG TCC GAT TTG CCA CAT CTA AAA CAG         136
Ala Val Ser Leu Trp Ala Leu Ser Asp Leu Pro His Leu Lys Gln
                 35                  40                  45

CTT GTC ATC AAT GAT TGC AAT GCC GAT TTA ATC AAT GTT TAT CAA         181
Leu Val Ile Asn Asp Cys Asn Ala Asp Leu Ile Asn Val Tyr Gln
                 50                  55                  60
```

```
GTT ATT AAA AAC AAC CCC GAT GAT TTG ATA GGA TAT ATT GAA AAT      226
Val Ile Lys Asn Asn Pro Asp Asp Leu Ile Gly Tyr Ile Glu Asn
             65                  70                  75

TTG CAA AGT CAT TAT GAT AAA TTA ACT GAT TTA GAA AGT AAA AAA      271
Leu Gln Ser His Tyr Asp Lys Leu Thr Asp Leu Glu Ser Lys Lys
             80                  85                  90

CCT TAT TTT TAT CAC AAA CGA GAT GTT TTT AAT CAA AGA ACC AGT      316
Pro Tyr Phe Tyr His Lys Arg Asp Val Phe Asn Gln Arg Thr Ser
             95                 100                 105

AAT GAT ATT GAG CAG GCA GGG TTA TTT ATC TTT TTA AAC AAA TCT      361
Asn Asp Ile Glu Gln Ala Gly Leu Phe Ile Phe Leu Asn Lys Ser
            110                 115                 120

GCT TTT AAT GGC TTA TAT CGT GTT AAT AAA AAT AAT CAA TTC AAC      406
Ala Phe Asn Gly Leu Tyr Arg Val Asn Lys Asn Asn Gln Phe Asn
            125                 130                 135

GTT CCC ATT GGT AAT TAT AAA AAA CCA ACT TTT GTA GAT AAA GAA      451
Val Pro Ile Gly Asn Tyr Lys Lys Pro Thr Phe Val Asp Lys Glu
            140                 145                 150

AAT ATT TTA AAT ATT TCA AAA AAA CTA CAA AAC ACC AAA ATA CTA      496
Asn Ile Leu Asn Ile Ser Lys Lys Leu Gln Asn Thr Lys Ile Leu
            155                 160                 165

TCA GGT GAT TTT GAA TTG GTT TTG GCT CAT TTG CCA AAT AAT TTT      541
Ser Gly Asp Phe Glu Leu Val Leu Ala His Leu Pro Asn Asn Phe
            170                 175                 180

CCC TGC CTA TTT TAC CTT GAT CCG CCT TAT CGT CCG ATT AGT GAT      586
Pro Cys Leu Phe Tyr Leu Asp Pro Pro Tyr Arg Pro Ile Ser Asp
            185                 190                 195

ACC GCA AGT TTT ACT TCT TAT TCT GAT AAT GGC TTT GAT GAT AAT      631
Thr Ala Ser Phe Thr Ser Tyr Ser Asp Asn Gly Phe Asp Asp Asn
            200                 205                 210

GAA CAA AAA CGC TTG GCA AAT TTT TGT AAA AAA ATA GAT AAG TTG      676
Glu Gln Lys Arg Leu Ala Asn Phe Cys Lys Lys Ile Asp Lys Leu
            215                 220                 225

GGT CAT TAT TTT TTA TTA AGC AAT TCC GAT CCA AAA AAT ACC AAT      721
Gly His Tyr Phe Leu Leu Ser Asn Ser Asp Pro Lys Asn Thr Asn
            230                 235                 240

TCA TCT GAT GAA TTT TTT GAT GAA TTA TAT CAA GAT TTT AAA ATT      766
Ser Ser Asp Glu Phe Phe Asp Glu Leu Tyr Gln Asp Phe Lys Ile
            245                 250                 255

GAG AGA ATA CAA GCT AAC CGC ACC ATT AGT GCC AAT AGT AAT GGT      811
Glu Arg Ile Gln Ala Asn Arg Thr Ile Ser Ala Asn Ser Asn Gly
            260                 265                 270

CGC AAA AAG GTA AAT GAA ATT ATA GTC AGT AAC GGA GTT TAAC ATG     857
Arg Lys Lys Val Asn Glu Ile Ile Val Ser Asn Gly Val      Met
            275                 280                      1

AAA TTA GCA TTT GAT GAT TTT TTA AAT AGT ATG TCA GAA ACC AAT      902
Lys Leu Ala Phe Asp Asp Phe Leu Asn Ser Met Ser Glu Thr Asn
              5                  10                  15

ACT ACT TTG GAT TAT TTT ACT GAT TTT GAT AAA GTA AAA AAG AAT      947
Thr Thr Leu Asp Tyr Phe Thr Asp Phe Asp Lys Val Lys Lys Asn
             20                  25                  30

GTC GCT CAA ATT GAG ATT CAC TTA AAC CAG CTT AAT TAT TTA TTG      992
Val Ala Gln Ile Glu Ile His Leu Asn Gln Leu Asn Tyr Leu Leu
             35                  40                  45

GGA AAA GAT GAT TTA AAA CAA GCA GTT TAT GAT TTA TAC GCC GAA     1037
Gly Lys Asp Asp Leu Lys Gln Ala Val Tyr Asp Leu Tyr Ala Glu
             50                  55                  60

TGC CCA AAT GCG TTT TCT ATC TTA GAA ATA CTG ATT GCA GTT AGA     1082
Cys Pro Asn Ala Phe Ser Ile Leu Glu Ile Leu Ile Ala Val Arg
             65                  70                  75

AAA AAG GAA CAA AAG AAA AGC CTA GAT GAA AAA GGT CAA GTG GTA     1127
Lys Lys Glu Gln Lys Lys Ser Leu Asp Glu Lys Gly Gln Val Val
```

-continued

| | | | | | | | | 80 | | | | | | 85 | | | | | | 90 | | | | |
|---|---|---|---|---|---|---|---|---|---|---|---|---|---|---|---|---|---|---|---|---|---|---|---|---|

```
ACA TTA AAT AGC TAC TTT CAA TCA GCA GAT AAA ATT ATA GAT TTT         1172
Thr Leu Asn Ser Tyr Phe Gln Ser Ala Asp Lys Ile Ile Asp Phe
         95              100                      105

CTT AAC AAT ACA GGG CTT GCT GAT GTA TTT AGA GAT AAA AAC ATC         1217
Leu Asn Asn Thr Gly Leu Ala Asp Val Phe Arg Asp Lys Asn Ile
        110                  115                     120

AAA AAT TTA GTT GAT TAT GTG TTT GGC ATT GAA GTG GGT TTG GAT         1262
Lys Asn Leu Val Asp Tyr Val Phe Gly Ile Glu Val Gly Leu Asp
        125                  130                     135

ACT AAT GCC CGA AAA AAT CGT GGT GGA GAC AAT ATG TCA AAA GCT         1307
Thr Asn Ala Arg Lys Asn Arg Gly Gly Asp Asn Met Ser Lys Ala
        140                  145                     150

GTT CAA TTA TTA TTT GAC AAT GCA GAT ATT TAT TAT AAA AAA GAA         1352
Val Gln Leu Leu Phe Asp Asn Ala Asp Ile Tyr Tyr Lys Lys Glu
        155                  160                     165

GTC AGA AAC ACC ATT TTT ACA GAC ATT GAA AGC TTG GGA GCT GAT         1397
Val Arg Asn Thr Ile Phe Thr Asp Ile Glu Ser Leu Gly Ala Asp
        170                  175                     180

GTC AAA CAA TTT GAT TTT GTC ATC AAA ACC AAA AGA AAA ACC TAT         1442
Val Lys Gln Phe Asp Phe Val Ile Lys Thr Lys Arg Lys Thr Tyr
        185                  190                     195

GTA ATT GAA ACC AAT TAT TAT AAT AGT GGT GGC TCA AAA TTA AAT         1487
Val Ile Glu Thr Asn Tyr Tyr Asn Ser Gly Gly Ser Lys Leu Asn
        200                  205                     210

GAA GTT GCC AGA GCT TAT ACT GAT GTT GCC CCA AAA ATC AAT CAA         1532
Glu Val Ala Arg Ala Tyr Thr Asp Val Ala Pro Lys Ile Asn Gln
        215                  220                     225

TAT TCG CAG TAT GAA TTT GTT TGG ATT ACC GAT GGT CAA GGC TGG         1577
Tyr Ser Gln Tyr Glu Phe Val Trp Ile Thr Asp Gly Gln Gly Trp
        230                  235                     240

AAA ACT GCC AAG AAT AAA CTA CAA GAA GCC TAT ACT CAT ATA CCT         1622
Lys Thr Ala Lys Asn Lys Leu Gln Glu Ala Tyr Thr His Ile Pro
        245                  250                     255

TCT GTT TAT AAT TTA TAT ACT TTG CAT GGT TTT ATT GAA CAG CTA         1667
Ser Val Tyr Asn Leu Tyr Thr Leu His Gly Phe Ile Glu Gln Leu
        260                  265                     270

AAT AGC GAA GGT GTT ATA AAG GAT TGG TAAA ATG AGA ATA AAA CCT        1713
Asn Ser Glu Gly Val Ile Lys Asp Trp      Met Arg Ile Lys Pro
        275                  280             1               5

TAT TTT GAA TCA GAT GAT AAA AAC TTT AAT ATC TAC CAG GGG AAT         1758
Tyr Phe Glu Ser Asp Asp Lys Asn Phe Asn Ile Tyr Gln Gly Asn
             10                  15                      20

TGC ATT GAT TTT ATG TCG CAT TTC AGG ATA AT TCC ATA GAT ATG         1803
Cys Ile Asp Phe Met Ser His Phe Gln Asp Asn Ser Ile Asp Met
             25                  30                      35

ATA TTT GCC GAT CCG CCC TAT TTT TTA TCC AAT GAT GGA TTA ACT         1848
Ile Phe Ala Asp Pro Pro Tyr Phe Leu Ser Asn Asp Gly Leu Thr
          40                   45                       50

TTT AAA AAT AGC ATT ATT CAA TCG GTT AAT AAA GGC GAA TGG GAT         1893
Phe Lys Asn Ser Ile Ile Gln Ser Val Asn Lys Gly Glu Trp Asp
           55                   60                      65

AAA AAT GAC AAT GAA GCT AGT ATT TAT AAT TTT AAT CAT GAA TGG         1938
Lys Asn Asp Asn Glu Ala Ser Ile Tyr Asn Phe Asn His Glu Trp
          70                    75                      80

ATA GCA CAA GCC AGA CAA TTA TTA AAA GAT AAC GGA ACC ATT TGG         1983
Ile Ala Gln Ala Arg Gln Leu Leu Lys Asp Asn Gly Thr Ile Trp
          85                   90                       95

ATA AGT GGT ACG CAC CAT AAT ATT TTT ACC GTT GGT CAA GTA TTA         2028
Ile Ser Gly Thr His His Asn Ile Phe Thr Val Gly Gln Val Leu
         100                  105                      110
```

| | | | | | | | | | | | | | | | |
|---|---|---|---|---|---|---|---|---|---|---|---|---|---|---|---|
| AAA | GAA | AAT | AAT | TTT | AAA | ATA | TTA | AAT | ATA | ATA | ACT | TGG | GAA | AAA | 2073 |
| Lys | Glu | Asn | Asn | Phe 115 | Lys | Ile | Leu | Asn | Ile 120 | Ile | Thr | Trp | Glu | Lys 125 | |
| CCT | AAT | CCA | CCG | CCT | AAT | TTT | TCT | TGC | CGT | TAT | TTT | ACC | TAT | TCA | 2118 |
| Pro | Asn | Pro | Pro 130 | Pro | Asn | Phe | Ser | Cys | Arg 135 | Tyr | Phe | Thr | Tyr | Ser 140 | |
| AGT | GAA | TGG | ATA | ATT | TGG | GCA | AGA | AAA | CAT | TCT | AAG | ATA | CCA | CAT | 2163 |
| Ser | Glu | Trp | Ile | Ile 145 | Trp | Ala | Arg | Lys | His 150 | Ser | Lys | Ile | Pro | His 155 | |
| TAT | TTT | AAC | TAT | GAT | TTG | ATG | AAA | AAA | TTA | AAT | GGC | GAC | AAA | CAA | 2208 |
| Tyr | Phe | Asn | Tyr | Asp 160 | Leu | Met | Lys | Lys | Leu 165 | Asn | Gly | Asp | Lys | Gln 170 | |
| CAA | AAA | GAC | ATA | TGG | CGA | TTG | CCT | GCG | GTG | GGC | AGT | TGG | GAA | AAG | 2253 |
| Gln | Lys | Asp | Ile | Trp 175 | Arg | Leu | Pro | Ala | Val 180 | Gly | Ser | Trp | Glu | Lys 185 | |
| ACA | CAG | GGT | AAA | CAC | CCT | ACT | CAA | AAA | CCA | CTT | GGG | CTT | TTA | TCT | 2298 |
| Thr | Gln | Gly | Lys | His 190 | Pro | Thr | Gln | Lys | Pro 195 | Leu | Gly | Leu | Leu | Ser 200 | |
| CGC | ATT | ATC | TTA | TCA | TCA | ACC | CAA | AAA | GAT | GAT | TTG | ATT | TTA | GAT | 2343 |
| Arg | Ile | Ile | Leu | Ser 205 | Ser | Thr | Gln | Lys | Asp 210 | Asp | Leu | Ile | Leu | Asp 215 | |
| CCA | TTT | TCA | GGC | TCT | GGC | ACA | ACA | GGT | ATT | GCT | GGT | GTA | TTG | TTG | 2388 |
| Pro | Phe | Ser | Gly | Ser 220 | Gly | Thr | Thr | Gly | Ile 225 | Ala | Gly | Val | Leu | Leu 230 | |
| GAT | AGA | AAT | TAT | ATC | GGT | ATT | GAG | CAA | GAA | TTA | GAG | TTT | TTA | GAG | 2433 |
| Asp | Arg | Asn | Tyr | Ile 235 | Gly | Ile | Glu | Gln | Glu 240 | Leu | Glu | Phe | Leu | Glu 245 | |
| TTA | TCA | AAA | AGG | CGT | TAT | CAC | GAA | ATC | ACA | CCT | GTA | TTA | AAA | AAT | 2478 |
| Leu | Ser | Lys | Arg | Arg 250 | Tyr | His | Glu | Ile | Thr 255 | Pro | Val | Leu | Lys | Asn 260 | |
| GAA | TTT | AAA | CAA | AAA | ATT | CGT | AAG | CAG | ATT | AGT | GCT | ATT | | | 2517 |
| Glu | Phe | Lys | Gln | Lys 265 | Ile | Arg | Lys | Gln | Ile 270 | Ser | Ala | Ile | | | |

| | | | | |
|---|---|---|---|---|
| TAATTGCAAT | TAAGTCCTTA | ACCACCCTAA | ACACCACACT | ACGCCCCTGT ACAATGACAT | 2577 |
| CAATATCAGG | GGCGTANAAA | AATCCATTTG | CCAACTCCAT | AAATTTTGT TAAAATTTGA | 2637 |
| TTTATTATTT | TTGGCTCTGG | TC | | | 2659 |

( 2 ) INFORMATION FOR SEQ ID NO:4:

( i ) SEQUENCE CHARACTERISTICS:
        ( A ) LENGTH: 256 base pairs
        ( B ) TYPE: nucleic acid
        ( C ) STRANDEDNESS: double
        ( D ) TOPOLOGY: linear     ( i i ) MOLECULE TYPE: genomic DNA     ( i i i ) HYPOTHETICAL:

( i v ) ANTI-SENSE:

( v ) FRAGMENT TYPE:

( v i ) ORIGINAL SOURCE:
        ( A ) ORGANISM: Moraxella bovis
        ( B ) STRAIN: 10900
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

(v i i i) POSITION IN GENOME:
    (A) CHROMOSOME/SEGMENT:
    (B) MAP POSITION:
    (C) UNITS:

(i x) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO:4:

```
AAGTTGCCGA GTTAGAAGGC AAATTAGGGA GATTGAGAAG CAGGTGGGGC AGTTGATAGT      60

TTGTAATCCC AACAACGGCA AATAGATTAT TTATAATCTA TTTGCTTAAT GCACCACTTA     120

ATGATGAAAA AAGTAA ATG AAA CCT TTT ATA AAA TGG GCG GGC GGT             166
                  Met Lys Pro Phe Ile Lys Trp Ala Gly Gly
                    1               5                  10

AAG AAT TCT TTG CTT GAT GAA ATT CAA AAA CGC TTG CCT GAT TTT           211
Lys Asn Ser Leu Leu Asp Glu Ile Gln Lys Arg Leu Pro Asp Phe
                15                  20                  25

GTT CAC TCA CAA GAT TTT TGT TTG GTA GAG CCT TTT GTT GGT GGT           256
Val His Ser Gln Asp Phe Cys Leu Val Glu Pro Phe Val Gly Gly
                30                  35                  40
```

MBOI RESTRICTION-MODIFICATION GENES

FIELD OF INDUSTRIAL APPLICATION

This invention relates to a restriction enzyme and a modification enzyme which are useful as a reagent in the field of genetic engineering. More particularly, it relates to an MboI restriction-modification genes and a method for producing MboI restriction and/or modification enzymes.

Prior Art

Since MboI restriction-modification enzymes were isolated from *Moraxella boris* ATCC 10900 in 1976, biochemical studies thereon have been conducted. The MboI restriction-modification enzymes consist of an MboI restriction enzyme having an activity of cleaving DNA and an MboI modification enzyme capable of protecting DNA from the cleavage by the MboI restriction enzyme. The MboI restriction enzyme is a typical type II restriction enzyme which recognizes a sequence consisting of four bases (5'-GATC-3') in a symmetric structure in a DNA sequence and cleaves the 5'-side of G in the recognition sequence in such a manner as to give a fragment with a protruding 5' end.

On the other hand, the MboI modification enzyme is an enzyme which has an ability to protect DNA from the cleavage by the MboI restriction enzyme by methylating A in the above recognition sequence.

Examples of known processes for producing the MboI restriction enzyme include one reported by Gelinas. He established a process for recovering the MboI restriction enzyme from the above *Moraxella boris* ATCC 10900 (hereinafter referred to simply as the Mbo strain). This process is described in *Journal of Molecular Biology*, 114, 169 (1977). There has hitherto been reported no well-established, detailed process for producing the MboI modification enzyme.

However, only a small amount of the MboI restriction enzyme and the MboI modification enzyme was obtained from the Mbo strain and it was difficult to obtain a large amount of these enzymes. Further, since the Mbo strain produced an MboII restriction enzyme and an MboII modification enzyme simultaneously in addition to the MboI restriction enzyme and the MboI modification enzyme, a complicated procedure was to produce exclusively the MboI restriction enzyme and the MboI modification enzyme. Meanwhile, Bocklage et al. reported a process for isolating MboII restriction-modification genes and cloning by ligating these genes into various vectors [see *Nucleic Acids Research*, 19, 1007 (1991)], but MboI restriction-modification genes have not been clarified so far.

Problems to be solved by the invention

It is an object of the present invention to provide MboI restriction-modification genes, to create a novel microorganism, in particular *Escherichia coli* which carries plasmids having, integrated thereinto, MboI restriction-modification genes and is suitable for the industrial production of the MboI restriction enzyme and the MboI modification enzyme, and to provide a process for producing the MboI restriction enzyme and the MboI modification enzyme by using this microorganism.

Means for solving the problems

To sum up, the present invention relates to MboI restriction-modification genes. The present invention also relates to a method for producing MboI restriction enzyme which comprises cultivating a microorganism carrying plasmids having, integrated thereinto, MboI restriction-modification genes, and recovering the MboI restriction enzyme thus produced from the culture.

The MboI restriction-modification genes involve a gene coding for the MboI restriction enzyme which has an activity of cleaving DNA and another gene coding for the MboI modification enzyme which has an ability to protect DNA from the cleavage by the MboI restriction enzyme.

The term "restriction-modification genes" as used herein means genes involving both of the restriction and modification enzyme genes as well as each of these genes. In other words, this term implies restriction and-/or modification enzyme genes. Either one of these enzymes or a complex thereof may be used herein.

When plasmids having, integrated thereinto, both of the above genes are to be used, these genes may be integrated either into the same plasmid or separately into a number of plasmids.

The present inventors have succeeded in cloning DNA fragments containing MboI restriction-modification genes from the Mbo strain and, further, found out that, when a microorganism, in particular, *E. coli* carrying plasmids in which either the whole or part of these DNA fragments are integrated either into the same plasmid or separately into a number of plasmids is cultivated, a considerable amount of the MboI restriction enzyme and/or the MboI modification enzyme are accumulated in the cells and a large amount of the MboI restriction enzyme and/or the MboI modification enzyme can be isolated from the culture, thus completing the present invention.

Now, the present invention will be described in greater detail.

The novel microorganism according to the present invention, for example, *E. coli* may be obtained by the following steps which are given by way of example.

(1) Chromosomal DNA is extracted from the Mbo strain functioning as a DNA donor. Then a product of partial digestion of the chromosomal DNA with a restriction enzyme is ligated into a vector which has been previously cleaved with restriction enzymes having the recognition sequence of the MboI restriction enzyme.

(2) An *E. coli dam* mutant is transformed by the plasmid library prepared in the above step (1) and a plasmid library which has not been dam-methylated is obtained by the plasmid extraction method.

(3) The plasmid library prepared in the above step (2) is cleaved with the MboI restriction enzyme and uncleaved plasmids, namely, those in which the MboI modification enzyme is expressed are selected.

(4) The MboI restriction enzyme is purified from the Mbo strain by Gelinas' method as described above. Then the amino acid sequence of this protein is partially determined from, for example, the N-terminal side and a DNA corresponding thereto is synthesized.

(5) Chromosomal DNA is extracted from the Mbo strain functioning as a DNA donor. Then the product of complete digestion of the chromosomal DNA with a restriction enzyme is subjected to Southern hybridization by using the DNA synthesized in the above step (4)

as a probe and a DNA fragment containing the same sequence as that of the probe DNA is selected.

(6) The DNA fragment selected in the above step (5) is ligated into a plasmid cleaved with restriction enzymes. Then the plasmid thus obtained, which contains at least part of the restriction enzyme gene, and the plasmid selected in the above step (3), which contains the modification enzyme gene, are introduced into *E. coli* via transformation.

(7) The activities of the MboI restriction enzyme and the MboI modification enzyme of the transformant prepared in the above step (6) are analyzed and thus a novel microorganism capable of producing the restriction enzyme and the modification enzyme is obtained.

The chromosomal DNA of the Mbo strain is extracted from the cells recovered from the culture. The extraction, purification and cleavage with restriction enzymes of the chromosomal DNA of the Mbo strain can be done by any of well-known methods which are described in detail by Thomas et al., "Procedures in Nucleic Acids Research", page 535, published by Harper and Row (1966); and Sambrook et al., "Molecular Cloning", published by Cold Spring Harbor Laboratory (1989).

On the other hand, the plasmid vectors can be cleaved by similar methods. Usable plasmids involve well-known ones, for example, pBR322. The plasmid pBR322 contains the recognition sequence of the MboI restriction enzyme and the MboI modification enzyme gene can be easily screened by using it.

The chromosomal DNA is ligated into the vector by well-known methods.

A detailed description of the process for introducing plasmids into an *E. coli* host is reported by, for example, Hanahan in *Journal of Molecular Biology*, 166, 577 (1983).

Plasmids are prepared from an *E. coli* host by the alkali method. From among the plasmids thus prepared, those which code for the MboI modification enzyme gene and have been already expressed can be selected because they are protected from the cleavage by the MboI restriction enzyme. As a result, plasmids containing a DNA fragment of approximately 4 kb originating in the Mbo strain are selected.

The amino acid sequence of enzyme protein is determined by transferring the purified protein onto a polyvinylidene difluoride (PVDF) membrane and analyzing on an automatic amino acid sequencer. This method is one reported by Paul Matsudaira in *Journal of Biological Chemistry*, 262, 10035 (1987). The SEQ ID No. 1 in the sequence listing represents the N-terminal amino acid sequence of the MboI restriction enzyme. Based on this amino acid sequence, a probe DNA, for example, the DNA represented by SEQ ID No. 2 in the sequence listing can be synthesized.

The southern hybridization is carried out by well-known methods. The DNA fragment thus obtained has a sequence complementary to the probe DNA. Namely, this fragment contains at least part of the MboI restriction enzyme gene.

Next, this DNA fragment must be analyzed in greater detail to thereby confirm whether or not the whole of the target restriction enzyme gene is integrated thereinto. The confirmation is carried out as follows. The DNA fragment seemingly containing the MboI restriction enzyme gene thus obtained is ligated into vector plasmid cleaved previously with restriction enzymes. The plasmid thus prepared and another plasmid containing the MboI modification enzyme gene which has been already obtained are then introduced into *E. coli* via transformation to thereby create a novel microorganism, and analyzing the MboI restriction enzyme activity of the novel microorganism thus obtained.

The MboI restriction enzyme activity can be examined by the following in vitro method. A clone to be examined is cultivated and the cells are disrupted and ultracentrifuged. After removing the debris, the supernatant is subjected to a restriction enzyme reaction at 37° C. in a buffer solution [10 mM Tris-HCl (pH 8.0), 7 mM $MgCl_2$, 150 mM KCl, 7 mM 2-mercaptoethanol, and 0.01% BSA] by using a non-dam-methylated DNA as a substrate, followed by the analysis by agarose gel electrophoresis. When analyzed by this method, the above novel microorganism was found to exhibit an MboI restriction enzyme activity. Based on this fact, it is confirmed that the MboI restriction-modification genes have been successfully isolated.

A plasmid containing a DNA fragment coding for the MboI modification enzyme gene originating in the Mbo strain is named pMMboI, while another plasmid containing a DNA fragment coding for the MboI restriction enzyme gene originating in the Mbo strain is named pRMboI. A novel microorganism obtained by integrating these plasmids and a plasmid pNT203 [see Gene, 29, 199–209 (1984)] into, for example, *E. coli* MC1061 strain by the transformation method is named *Escherichia coli* MC1061/pMboI and deposited with Fermentation Research Institute of the Agency of Industrial Science and Technology under the accession number FERM P-12717.

The DNA sequences of the DNA fragments inserted into pMMboI and pRMboI can be determined by, for example, preparing deletion mutants in accordance with the method of Yanisch-Perron and then effecting dideoxy method. As a result, it is found out that the DNA fragments inserted into pMMboI and pRMboI partially overlap with each other. That is, the DNA fragments inserted into pMMboI and pRMboI are in succession. The SEQ ID No. 3 in the sequence listing shows this DNA sequence. In the DNA sequence represented by SEQ ID No. 3 in the sequence listing, namely, the part represented by the bases Nos. 1-2222 is inserted into pRMboI, while the part represented by the bases Nos. 1666-2659 is inserted into pMMboI. Further, open reading frees (ORF) can be detected by using, for example, DNASIS ™ (Takara Shuzo). As a result, it is found out that ORFs are located in three parts, namely, the bases Nos. 1–850, the bases Nos. 855–1694 and the bases Nos. 1699–2517 in the DNA sequence represented by the SEQ ID No. 3 in the sequence listing and these ORFs are respectively named mboA, mboB, and mboC.

Based on the fact that pMMboI contains mboC alone, it is determined that mboC is a gene coding for the MboI modification enzyme. Since the amino acid sequence presumed based on the mboB gene is identical with the N-terminal amino acid sequence of the MboI restriction enzyme protein represented by the SEQ ID No. 1 in the sequence listing, it is determined that mboB is a gene coding for the MboI restriction enzyme.

After removing the region coding for mboC from pRMboI, the resultant plasmid (pRMboID) is introduced into *E. coli* and then the activity of the MboI modification enzyme in vivo is measured. As a result, a modification activity is observed and, therefore, it is determined that the mboA gene codes for the MboI modification enzyme.

The mboA gene contained in the DNA fragment originating in the Mbo strain and inserted into pRMboI is thought to lack the 5' side, since it contains no initiation codon. Thus, the region located in the further upstream is isolated by performing the plaque hybridization with the use of the above oligonucleotide represented by the SEQ ID No. 2 in the sequence listing as a probe. Then the obtained clone having a sequence homologous with that of the probe contains a DNA of about 5.1 kb originating in the Mbo strain. When part of the DNA sequence of this DNA fragment is determined, it is found that this DNA fragment contains the whole region of about 2.1 kb containing the MboI restriction enzyme gene inserted into pRMboI. Further, the DNA sequence of the upstream of the mboA gene is clarified. The DNA sequence is shown by the bases Nos. 1–168 in the DNA sequence represented by the SEQ ID No. 4 in the sequence listing.

In order to cultivate the novel microorganism thus obtained, ordinary conditions suitable for the growth of microorganisms belonging to the genus *Escherichia* can be employed.

In order to cultivate the above recombinant *Escherichia coli* MC1061/pMboI and to recover the MboI restriction enzyme and MboI modification enzymes from the culture, the cells are collected from the culture and the enzymes are extracted by, for example, ultrasonication or ultracentrifugation and then purified by combining purification techniques such as nucleic acid removal, salting out, affinity chromatography, gel filtration and ion-exchange chromatography. Thus, a large amount of the MboI restriction enzyme and/or MboI modification enzyme can be obtained.

EXAMPLE

In order to illustrate the present invention in greater detail, and not by way of limitation, the following Examples will be given.

EXAMPLE 1

(1) Preparation of Chromosomal DNA from Mbo Strain The Mbo strain was cultivated in 100 ml of an L+BHI medium (10 g/l trypton, 5 g/l yeast extract, 5 g/l sodium chloride, and 5 g/l brain heart infusion) at 37° C. overnight and cells were collected by centrifugation. The cells were suspended in 10 ml of a 25 mM Tris-HCl (pH 8.0)-50 mM glucose-10 mM EDTA solution. Lysozyme was dissolved in the same solution in such a manner as to give a concentration of 2 mg/ml nd 1.0 ml of the resulting lysozyme solution was added to the above suspension. After stirring, the mixture was allowed to stand at 37° C. for 15 minutes. Next, 28 ml of a 100 mM NaCl-100 mM Tris-HCl (pH 8.0) solution was added thereto followed by stirring. Further, 4 ml of a 10% SDS solution was added and the mixture was stirred and allowed to stand at 37° C. for an hour. Then 1 ml of a 10% SDS-8% Sarcosyl solution was added thereto and the mixture was stirred and allowed to stand at 60° C. for 15 minutes. After allowing the solution to stand, the same volume of a mixture of phenol with chloroform (1:1) was added thereto. After slowly stirring for 10 minutes, the mixture was separated into an aqueous phase and a chloroform phase by centrifugation at 6,000 xg for 10 minutes. Then the aqueous phase was taken up and the same amount of isopropyl alcohol was added thereto. After stirring, the mixture was allowed to stand at 0° C. for 10 minutes and then centrifuged at 13,500 xg for 10 minutes. The precipitate thus formed was recovered, washed with 70% ethanol, dissolved in 10 ml of a TE solution [10 mM Tris-HCl (ph 8.0) and 1 mM EDTA] and stored at 4° C.

(2) Preparation of library

25 μg of the chromosomal DNA of the Mbo strain obtained in the above step (1) was reacted with 1 U of a restriction enzyme AluI in a buffer solution [10 mM Tris-HCl (ph 7.5), 10 mM $MgCl_2$, nd 1 mM dithiothreitol] at 37° C. for 1 to 10 minutes. Then the reaction mixture was electrophoresed on an agarose gel and fragments of 3 to 7 kb were recovered from the gel. These DNA fragments were ligated into pBR322, which had been previously cleaved with EcoRV, and then *E. coli* GM33 (dam⁻) was transformed by these plasmids. From the transformant thus obtained were prepared plasmids by the alkali method.

(3) Isolation of modification enzyme gene

When the plasmids obtained in the above step (2) were cleaved with the restriction enzyme MboI, those wherein the MboI modification enzyme had been expressed were not cleaved. Then *E. coli* GM33 was transformed by the obtained mixture consisting of cleaved DNAs and uncleaved ones. Thus the uncleaved plasmids were exclusively introduced into the *E. coli*. Next, a transformant was selected by using a plate containing ampicillin and thus a transformant containing the MboI modification enzyme gene was obtained.

(4) Analysis of modification enzyme gene

Figure 1:
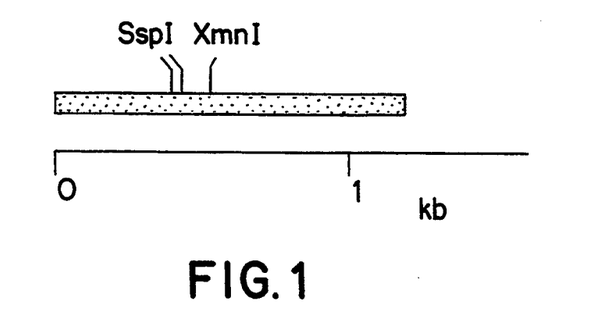
FIG. 1 shows the restriction enzyme map of a DNA of 1.2 kb containing the MboI modification enzyme gene.

The plasmid in which the MboI modification enzyme had been expressed contained a DNA fragment of about 4 kb originating in the Mbo strain. In order to specify the position of the MboI modification enzyme gene, deletion clones of this DNA fragment were prepared by digestion with Exonuclease III (Takara Shuzo) and Mung Bean Nuclease (Takara Shuzo) to thereby give plasmids having DNA fragments differing from each other in size and then the modification enzyme activities thereof were measured. As a result, it was found out that the MboI modification enzyme gene was located on a DNA fragment of about 1.2 kb represented by the restriction enzyme map of FIG. 1. This DNA fragment of 1.2 kb was ligated into a plasmid pACYC184 and the plasmid thus obtained was named pMMboI.

(5) Determination of the N-terminal amino acid sequence of MboI restriction enzyme protein and preparation of probe DNA The MboI restriction enzyme protein purified from the Mbo strain was electrophoresed on an SDS-polyacrylamide gel, transferred onto a PVDF membrane, stained with Coomassie brilliant blue R-250 and then decolored with 10% acetic acid-50% methanol. The MboI restriction enzyme protein band was cut out and sequenced by Edman's method with the use of an automatic amino acid sequencer to determine the N-terminal amino acid sequence represented by the SEQ ID No. 1 in the sequence listing.

Based on this sequence, a 23-meric oligonucleotide represented by the SEQ ID No. 2 was synthesized.

(6) Isolation of MboI restriction enzyme gene

Figure 2:
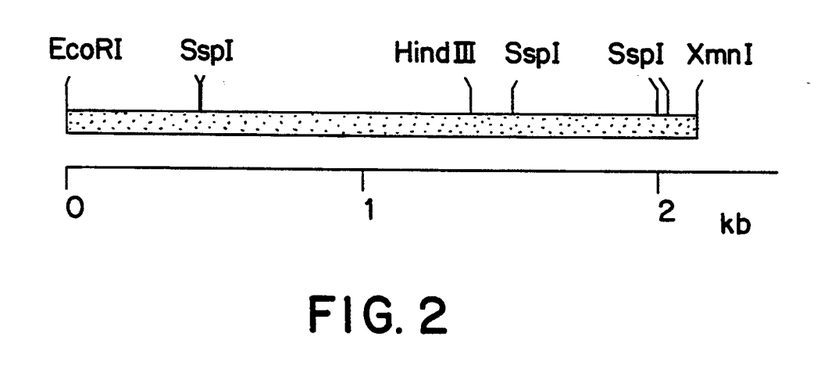
FIG. 2 shows the restriction enzyme map of a DNA of 2.1 kb containing the MboI restriction enzyme gene.

The chromosomal DNA of the Mbo strain was completely digested with various restriction enzymes and Southern hybridization was carried out by using the oligonucleotide represented by the SEQ ID No. 2 in the sequence listing as a probe. As a result, it was presumed that the EcoRi-XmnI fragment of 2.1 kb might have the same sequence as that of the probe DNA. Then 10 μg of the chromosomal DNA of the Mbo strain was digested with 100 U of restriction enzymes EcoRI and XmnI and electrophoresed on a 0.7% Seakem GTG agarose gel. Then a DNA fragment of 2.1 kb was adsorbed on DE paper and thus with drawn from the gel. Next, the DNA fragment was recovered by ethanol precipitation and an EcoRI linker was ligated thereinto. This DNA fragment was ligated into a vector λgt10, packaged and infected with an E. coli C600 (Hfl) strain. The plaques thus obtained were transferred onto a nitrocelulose membrane and the plaque hybridization was carried out by using the synthetic DNA obtained in the above step (5) as a probe. Thus a plaque having a sequence identical with that of the probe DNA was obtained. This recombinant λ phage DNA was prepared and the DNA fragment of about 2.1 kb originating in the Mbo strain, represented by the restriction enzyme map of FIG. 2 was cut out with a restriction enzyme EcoRI and ligated into the EcoRI site of a plasmid PpKHI described in *Proceedings of the National Academy of Sciences of the USA*, 80, 7137–7141 (1983) to thereby prepare a plasmid seemingly containing the MboI restriction enzyme gene. This plasmid was named pRMboI.

E. coli MC1061 was transformed by the plasmids pMMboI, pRMboI, and pNT203 and the MboI restriction enzyme activity was measured in vitro. As a result, the activity was observed. Thus the E. coli strain carrying these plasmids was named *Escherichia coli* MC1061/pMboI and deposited with Fermentation Research Institute of the Agency of Industrial Science and Technology under the accession number FERM P-12717.

(7) Analysis of the structure of MboI restriction-modification genes

The DNA sequences of the DNA fragments inserted into pMMboI and pRMboI were determined by preparing deletion mutants with the use of Exonuclease III (Takara Shuzo) and Mung Bean Nuclease (Takara Shuzo) and then effecting the dideoxy method. As a result, it was found out that the DNA fragments inserted into pMMboI and pRMboI partially overlapped with each other. That is, the DNA fragments inserted into pMMboI and pRMboI were in succession. The SEQ ID No. 3 in the sequence listing shows these successive DNA sequences. In the DNA sequence represented by the SEQ ID No. 3 in the sequence listing, namely, the part represented by the bases Nos. 1-2222 was inserted into pRMboI, while the part represented by the bases Nos. 1666-2659 was inserted into pMMboI.

Next, open reading frames (ORF) were detected by using DNASIS TM (Takara Shuzo). As a result, it was found out that ORFs were located in three parts, namely, the bases Nos. 1-850, the bases Nos. 855-1694 and the bases Nos. 1699-2517 in the DNA sequence represented by the SEQ ID No. 3 in the sequence listing and these ORFs were respectively named mboA, mboB and mboC. The SEQ ID No. 3 in the sequence listing shows the amino acid sequence corresponding to each of these ORFs.

(8) Analysis of mboA Gene pRMboI was cleaved with HindIII to thereby eliminate the mboC gene and then ligated to thereby give a plasmid pRMboID containing most of mboA and part of mboB. This plasmid was introduced into E. coli GM33 (dam−) via transformation and a plasmid was extracted from the transformant thus obtained. Then it was examined whether or not the obtained plasmid was cleaved with the MboI restriction enzyme. As a result, it was not cleaved, which indicated that the mboA gene coded for the MboI modification enzyme.

(9) Cloning of the Upstream Region of mboA Gene

The genomic DNA of the Mbo strain was completely digested with restriction enzymes BglII and XmnI and then end-blunted. After ligating to a linker EcoRI linker, it was inserted into a vector λgt10. The library thus obtained was introduced into E. coli via transfection and plaque hybridization was performed by using the oligonucleotide represented by the SEQ ID No. 2 in the sequence listing as a probe. The clone thus obtained, which had a sequence homologous with that of the probe, contained a DNA of about 5.1 kb originating in the Mbo strain. When the DNA sequence of this DNA fragment was partially determined, it was found that the region of about 2.1 kg containing the MboI restriction enzyme gene inserted into pRMboI was completely contained therein. Further, the DNA sequence of the upstream of the mboA gene was clarified. The DNA sequence is shown by the bases Nos. 1-168 in the DNA sequence represented by the SEQ ID No. 4 int he sequence listing.

EXAMPLE 2

(1) Production of MboI restriction enzyme by the transformant

The *Escherichia coli* MC1061/pMboI (FERM P-12717) obtained in the above Example 1-(6) was inoculated into 100 ml of an L medium containing 100 μg/ml of ampicillin and cultivated therein at 30° C. for six hours, at 42° C. for 15 minutes and then at 37° C. for six hours. Then the cells were collected and suspended in 1.2 ml of a 20 mM potassium phosphate buffer solution (pH 7.5) containing 10 mM of 2-mercaptoethanol and 0.15% of Triton X-100. After disrupting of the cells by ultrasonication, the supernatant was recovered by ultracentrifugation at 10,000 xg for 30 minutes. When the activities of the supernatant were measured, it was found out that 400,000 U of the MboI restriction enzyme and 8,000 U of the MboI modification enzyme were produced therein.

(2) Purification of MboI restriction enzyme

*Escherichia coli* MC1061/pMboI was inoculated into 2 liters of an L medium containing 100 μg/ml of ampicillin and cultivated therein at 30° C. for six hours, at 42° C. for 15 minutes and then at 37° C. for six hours. After collecting, 10 g of the wet cells were suspended in 20 ml of a 20 mM potassium phosphate buffer solution (pH 7.5) containing 10 mM of 2-mercaptoethanol and 0.15% of Triton X-100. After disruption of the cells by ultrasonication, the supernatant was recovered by ultracentrifugation at 10,000 xg for 30 minutes. Then the same amount of a buffer solution A [20 mM KPB (pH 7.5), 10 mM 2-mercaptoethanol, and 5% glycerol] was added thereto and the mixture was loaded on a phosphocellulose column equilibrated with the same buffer solution. Then it was developed by linear gradient elution with 0 to 1M potassium chloride and a fraction having an MboI restriction enzyme activity was recovered. Then, this fraction was dialyzed against a buffer solution B [10 mM KPB (pH 7.5), 10 mM 2-mercaptoethanol, and 5% glycerol] and loaded on an Affi-Gel Blue column (BIO RAD) equilibrated with the same buffer solution. Then it was developed by linear gradient elution with 0 to 0.75M potassium chloride and approximately 5 ml of a fraction having an MboI restriction enzyme activity was recovered. This fraction was dialyzed against the buffer solution B again and loaded on a heparin-Sepharose column. Next, it was developed by linear gradient elution with 0 to 1M potassium chloride. The fraction having an MboI restriction enzyme activity thus recovered was loaded on a Sephadex G-100 column. The enzymatic activity of the active fraction thus obtained corresponded to approximately 1,000,000 U. This purified preparation was not contaminated with any other enzyme such as endonuclease, phosphatase or nonspecific DNase.

(3) Purification of MboI modification enzyme

*Escherichia coli* MC1061/pMboI was inoculated into 2 liters of an L medium containing 100 μg/ml of ampicillin and cultivated therein at 30° C. for six hours, at 42° C. for 15 minutes and then at 37° C. for six hours. After collecting, 10 g of the wet cells were suspended in 30 ml of the buffer solution A. After disruption of the cells by ultrasonication, the supernatant was recovered by ultracentrifugation at 10,000 xg for 30 minutes. Then a streptomycin sulfate solution was added to the supernatant in such a manner as to give a concentration of 2%. After stirring, the supernatant was recovered by centrifugation. Next, an ammonium sulfate powder was added thereto in such a manner as to achieve 65% -saturation and then recovered by ultracentrifugation at 13,500 xg for 30 minutes. The precipitate thus recovered was suspended in the buffer solution B [10 mM KPB (pH 7.5), 10 mM 2-mercaptoethanol, and 5% glycerol] and dialyzed against the buffer solution B. Then it was loaded on a heparin-Sepharose column equilibrated with the buffer solution B and developed by linear gradient elution with 0.05 to 0.80M sodium chloride. A fraction having an MboI modification enzyme activity was recovered and dialyzed against the buffer solution B. Then it was loaded on a DEAE-Sephadex (A-50) column equilibrated with the buffer solution B and developed by linear gradient elution with 0.05 to 0.60M sodium chloride. Then a fraction having an MboI modification enzyme activity was recovered and dialyzed against the buffer solution B. Then it was loaded on a phospho-cellulose column which had been previously equilibrated with the buffer solution B and developed by linear gradient elution with 0.05 to 1.0M sodium chloride. The enzymatic activity of the active fraction thus obtained corresponded to approximately 30,000 U. This purified preparation was not contaminated with any other enzyme such as endonuclease, phosphatase or nonspecific DNase.

Effect of the Invention

As has been described above in detail, MboI restriction-modification genes are isolated according to the present invention. The use of an *E. coli* strain transformed with plasmids containing these genes makes it possible to produce the MboI restriction enzyme and/or MboI modification enzyme, which are useful in the field of genetic engineering, at a high efficiency.

---

What is claimed is:

1. Isolated DNA coding for the MboI restriction enzyme, wherein the isolated DNA is obtainable from the vector pRMboI.

2. A recombinant DNA vector comprising a vector into which a DNA segment coding for the MboI restriction enzyme produced by *Morexela bovis* ATCC 10900 has been inserted.

3. Isolated DNA coding for the MboI modification enzyme, wherein the isolated DNA is obtainable from the vector pRMboI or pMMboI.

4. A cloning vector which comprises the isolated DNA of claim 1.

5. A cloning vector which comprises the isolated DNA of claim 3.

6. A cloning vector of claim 4, wherein the cloning vector comprises pRMboI.

7. A host cell transformed by the vector of claim 4, 5, or 6.

8. A method of producing MboI restriction enzyme comprising culturing a host cell transformed with the vector of claim 4, 5, or 6 under conditions suitable for the expression of said enzyme.

* * * * *